(12) United States Patent
Grass et al.

(10) Patent No.: US 11,031,136 B2
(45) Date of Patent: Jun. 8, 2021

(54) ASSISTANCE DEVICE AND METHOD FOR AN INTERVENTIONAL HEMODYNAMIC MEASUREMENT

(71) Applicant: KONINKLIJKE PHILIPS N.V., Eindhoven (NL)

(72) Inventors: Michael Grass, Buchholz In der Nordheide (DE); Christian Haase, Hamburg (DE); Peter Maria Johannes Rongen, Eindhoven (NL); Roland Wilhelmus Maria Bullens, Mierlo (NL); Arjen Van Der Horst, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 343 days.

(21) Appl. No.: 15/745,162

(22) PCT Filed: Jul. 26, 2016

(86) PCT No.: PCT/EP2016/067725
§ 371 (c)(1),
(2) Date: Jan. 16, 2018

(87) PCT Pub. No.: WO2017/021201
PCT Pub. Date: Feb. 9, 2017

(65) Prior Publication Data
US 2018/0211729 A1 Jul. 26, 2018

(30) Foreign Application Priority Data

Aug. 5, 2015 (EP) .................................... 15179819

(51) Int. Cl.
*G16H 50/50* (2018.01)
*G16H 10/60* (2018.01)
*G06F 111/10* (2020.01)

(52) U.S. Cl.
CPC ............. *G16H 50/50* (2018.01); *G16H 10/60* (2018.01); *G06F 2111/10* (2020.01)

(58) Field of Classification Search
CPC ...... G16H 50/50; G16H 50/60; G06F 2111/10
(Continued)

(56) References Cited

U.S. PATENT DOCUMENTS 7,574,026 B2  8/2009 Rasche
8,157,742 B2  4/2012 Taylor
(Continued)

FOREIGN PATENT DOCUMENTS

DE  102008014792   6/2009
WO  00/72037   11/2000
(Continued)

OTHER PUBLICATIONS

Cheng_2008 (A computational fluid dynamic study of stent graft remodeling after endovascular repair of thoracic aortic dissections, 2008, The Society of Vascular Surgery). (Year: 2008).*
(Continued)

*Primary Examiner* — Brian S Cook
(74) *Attorney, Agent, or Firm* — Larry Liberchuk

(57) ABSTRACT

The invention relates to an assistance device, an assistance system and an assistance method for assisting a practitioner in an interventional hemodynamic (e.g fractional flow reserve (FFR)) measurement on a subject. The FFR pressure measurements are combined with an, for example, angiography-based assessment of the coronary vessel geometry. An advanced computational fluid dynamics model may be employed to add flow and myocardial resistance data based on the interventional pressure values and on a vascular model generated prior to the intervention. In case that these data are available prior to the intervention, the location of most optimal positions for pressure measurements can be
(Continued)

pre-calculated and by overlay of the vessel tree, for example, on the X-ray projection, advice can be given for the interventional cardiologist during the intervention.

14 Claims, 2 Drawing Sheets

(58) Field of Classification Search
USPC .............................................................. 703/2
See application file for complete search history.

(56) References Cited

U.S. PATENT DOCUMENTS

| | | | |
|---|---|---|---|
| 8,200,466 B2 | 6/2012 | Taylor | |
| 8,249,815 B2 | 8/2012 | Taylor | |
| 2010/0125197 A1 | 5/2010 | Fishel | |
| 2010/0130878 A1 | 5/2010 | Lasso | |
| 2010/0241404 A1 | 9/2010 | Taylor | |
| 2011/0071404 A1* | 3/2011 | Schmitt | A61B 5/0066 600/479 |
| 2011/0211742 A1 | 9/2011 | Bredno | |
| 2011/0307231 A1 | 12/2011 | Kirchner | |
| 2012/0022843 A1 | 1/2012 | Ionasec | |
| 2012/0041318 A1* | 2/2012 | Taylor | A61B 5/055 600/504 |
| 2012/0041319 A1 | 2/2012 | Taylor | |
| 2012/0041320 A1 | 2/2012 | Taylor | |
| 2012/0041321 A1 | 2/2012 | Taylor | |
| 2012/0041322 A1 | 2/2012 | Taylor | |
| 2012/0041323 A1 | 2/2012 | Taylor | |
| 2012/0041324 A1 | 2/2012 | Taylor | |
| 2012/0041325 A1 | 2/2012 | Taylor | |
| 2012/0041739 A1 | 2/2012 | Taylor | |
| 2012/0053919 A1 | 3/2012 | Taylor | |
| 2012/0059246 A1 | 3/2012 | Taylor | |
| 2012/0072190 A1 | 3/2012 | Sharma | |
| 2012/0121151 A1 | 5/2012 | Bernhardt | |
| 2012/0243761 A1 | 9/2012 | Senzig | |
| 2012/0296199 A1 | 11/2012 | Kim | |
| 2014/0114618 A1 | 4/2014 | Fonte | |
| 2015/0112191 A1 | 4/2015 | Gilboa | |

FOREIGN PATENT DOCUMENTS

| | | |
|---|---|---|
| WO | 2004025572 | 3/2004 |
| WO | 200661814 | 6/2006 |
| WO | 200661815 | 6/2006 |
| WO | 201022762 | 3/2010 |
| WO | 2013071219 | 5/2013 |
| WO | 2014111930 | 7/2014 |
| WO | 2014127320 | 8/2014 |
| WO | 2015/082576 | 6/2015 |

OTHER PUBLICATIONS

Liu_2004 (Catheter-Based Intraluminal Sonography, 2004 American Institute of Ultrasound in Medicine). (Year: 2004).*

Unit_Set_2015 (Set (Mathematics) Wikipedia Archived dated Aug. 2, 2015 downloaded from https://en.wikipedia.org/w/index.php?title=Set_(mathematics)&oldid=674281577 ). (Year: 2015).*

* cited by examiner

ASSISTANCE DEVICE AND METHOD FOR AN INTERVENTIONAL HEMODYNAMIC MEASUREMENT

CROSS REFERENCE TO RELATED APPLICATIONS

This application is the U.S. National Phase application under 35 U.S.C. § 371 of International Application No. PCT/EP2016/067725, filed Jul. 26, 2016, published as WO 2017/021201 on Feb. 9, 2017, which claims the benefit of European Patent Application Number 15179819.6 filed Aug. 5, 2015. These applications are hereby incorporated by reference herein.

FIELD OF THE INVENTION

The invention relates to an assistance device for assisting a practitioner in an interventional hemodynamic measurement (in particular a fractional flow reserve measurement) on a subject, and a corresponding software product.

BACKGROUND OF THE INVENTION

Invasive catheter-based pressure measurements are recently seeing increasing attention for functional stenosis assessment (e.g. in coronary arteries). Such measurements can be combined with a 3D vessel model and computational fluid dynamics calculations to deliver additional parameters like flow and myocardial resistance for a per branch analysis.

Apart from general guidelines and personal experience, little assistance is given to practitioners in such invasive measurements and, accordingly, the results of the overall procedure vary from patient to patient and from practitioner to practitioner, in particular in terms of reliability, completeness and significance.

SUMMARY OF THE INVENTION

It is an object of the present invention to allow for an improvement in reliability, completeness and significance of measurement results of, for example, interventional fractional flow reserve measurements, in particular in the case of invasive catheter-based pressure measurements for functional stenosis assessment.

In a first aspect of the present invention, an assistance device is presented for assisting a practitioner in an interventional hemodynamic measurement on a subject, comprising a model acquiring unit arranged to acquire a vessel model of vessel geometry of the subject, a position determination unit for determining a set of positions for hemodynamic measurements based on the vessel model complying with a predetermined metric, and an output unit for outputting the determined set of positions to the practitioner.

In a second aspect of the present invention, an assistance system is presented for assisting a practitioner in an interventional hemodynamic measurement on a subject, comprising the assistance device according to claim 1 and at least one of a data storage device storing image data of vessel geometry of the subject and a display device for displaying the determined set of positions to the practitioner.

In a third aspect of the present invention, an assistance method is presented for assisting a practitioner in an interventional hemodynamic measurement on a subject, comprising a model acquiring step of acquiring a vessel model of vessel geometry of the subject, a position determination step of determining a set of positions for hemodynamic measurements based on the vessel model complying with a predetermined metric, and an output step of outputting the determined set of positions to the practitioner.

The invention provides a technique related in particular to fractional flow reserve (FFR) measurement. The FFR pressure measurements are combined with an, for example, angiography-based assessment of the coronary vessel geometry. An advanced computational fluid dynamics model may be employed to add flow and myocardial resistance data based on the interventional pressure values and on a vascular model generated prior to the intervention. In case that these data are available prior to the intervention, the location of most optimal positions for pressure measurements can be pre-calculated and by overlay of the vessel tree, for example, on the X-ray projection, advice can be given for the interventional cardiologist during the intervention.

It was realized by the inventors, that, for example, for patients which had a pre-interventional coronary angiography using CT, the vessel tree can be segmented prior to the intervention and it can be overlaid on the projection during the intervention (CT overlay functionality). With the segmented vessel tree available during the intervention, advice can be given to the interventional cardiologist, at which positions and in which branches pressure measurements should be performed to achieve a most stable and complete functional characterization of the coronary artery tree. This may include measurement in different branches, proximal and distal to a stenosis or to branching vessels.

In a preferred embodiment, the position determination unit is arranged to provide a plurality of simulations using a lumped parameter model for computational fluid dynamics and the metric includes a stability of a solution including a set of positions.

The lumped parameter model allows for a convenient approach on modifying the conditions of the simulations. The stability of a solution is tested, for example, by varying pressure values at different positions in the vessel tree and testing the stability of the solution by analyzing the overall variation of the solution.

Model boundary conditions may be taken into consideration, as well as an accuracy of segmentation provided in obtaining the vessel model. Other parameters which may be used include the segmentation length resulting in different vessel radii at the outlets or the number of branches included.

In a modification of the above preferred embodiment, the position determination unit is arranged to obtain the stability of a solution by providing simulated pressure variations and/or flow variations at a plurality of positions in the vessel model.

In a preferred embodiment, the position determination unit is arranged to take into account information on a position and/or degree of a stenosis in the vessel of the subject.

Preferably, already available information on a stenosis of the subject is taken into consideration for optimization.

In a preferred embodiment, the predetermined metric includes a number of positions included in the set of positions.

The number of measurements needed for a complete characterization of the vessel tree impacts on the duration of the procedure and it is thus beneficial to reduce the number of measurement points by avoiding redundancies and the like. Depending on the particular details of the vessel, additional measurement points may be beneficial, as such information may be used to obtain flow information with a higher accuracy than at other positions. In other words, the additional measurement point may allow for an improved information gathering on global vessel data.

In a preferred embodiment, the position determination unit is further arranged to determine temporal information for at least one of the determined positions, the temporal information indicating a measurement time in relation to a predetermined reference. In a modification of this preferred embodiment, the predetermined reference is a cardiac phase of the subject.

In addition to a purely spatial measurement advice, temporal advice may also be given, e.g. by analyzing the projection sequence with respect to the cardiac phase (e.g. by correlation of the 3D model to the 2D projection or via the ECG).

In a preferred embodiment, the model acquiring unit is arranged to receive three-dimensional image data and/or a plurality of two-dimensional image data of the vessel geometry of the subject and to generate the vessel model based on the image data.

In an alternative to generating the vessel model by means of the model acquiring unit, the model acquiring unit may also be provided with such model from the outside, e.g. from a database including previously obtained information on the subject/patient.

In a modification of the above preferred embodiment, the model acquiring unit is arranged to receive a pre-interventional data set of the vessel geometry of the subject and to segment the data set for generating the vessel model.

A possible source of the data set may be computer tomography, which is an imaging approach which is widely spread and often employed, in particular in preparation for invasive FFR measurements. Other data source may include intravascular ultrasound (IVUS), optical coherence tomography (OCT) and magnetic resonance imaging (MRI). The data set may also be obtained by combinations of such methods.

In a preferred embodiment, the vessel model is one of a lumen and centerline model, a tetrahedral model representing the coronary lumen volume as tetrahedrons and a voxelized model. From these the lumen and centerline model or the tetrahedral model are preferred for convenience in the simulation procedures.

It is possible to use full 3D models, a combination of lumped model for a selected subset of the vessel sections (e.g. healthy vessel section) with a full 3D model for the stenosed sections, and/or a 1D wave propagation model (e.g. spectral elements) of the healthy part and specific stenosis model for the stenosis model.

In a preferred embodiment, the output unit is arranged to register the vessel model with one or more invasive angiograms and to cause a display of the determined set of positions in an overlay onto a projection during intervention.

An advantageous approach for displaying the determined positional (and perhaps additional temporal) information for optimization of the measurement includes the overlay of the information, so the practitioner may observe and use the information during the procedure in a convenient way.

In a further aspect of the present invention a computer program is presented for assisting a practitioner in an interventional hemodynamic measurement on a subject, the software product comprising program code means for causing an assistance device according to the present invention to carry out the steps of the method according to the present invention when the software product is run on the assistance device.

It shall be understood that the assistance device of claim 1, the assistance system of claim 12, the assistance method of claim 13, and the computer program of claim 14 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
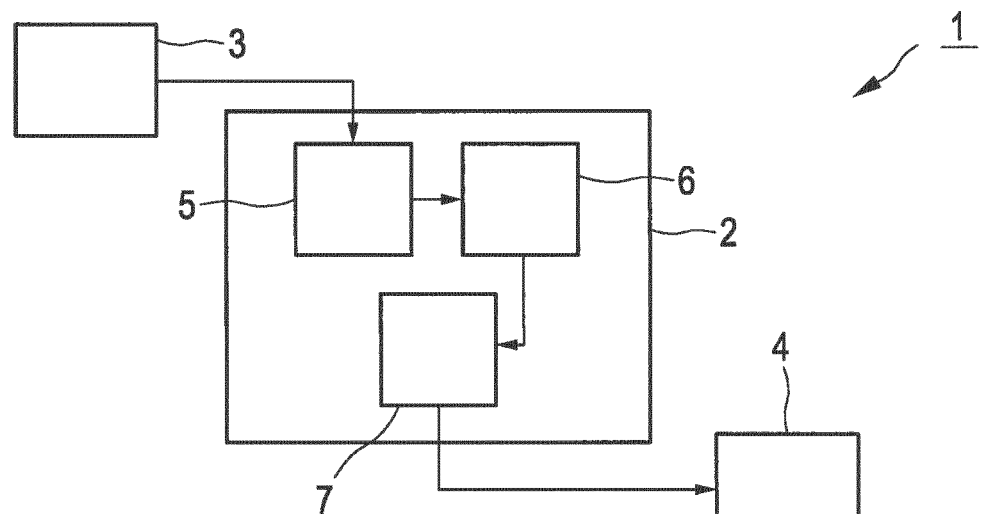
FIG. 1 shows an assistance system including an assistance device in accordance with an embodiment of the invention.

FIG. 1 shows an assistance system 1 including an assistance device 2 in accordance with an embodiment of the invention.

The assistance system 1 includes the assistance device 2, a data storage device 3 and a display device 4. The data storage device 3 stores image data of vessel geometry of the subject, in particular pre-interventional coronary angiography data obtained using computer tomography. The image data is provided to the assistance device 2, which, in turn, outputs information to be displayed to the practitioner carrying out the interventional fractional flow reserve measurement to the display device 4.

The assistance device 2 includes a model acquiring unit 5, a position determination unit 6 and output unit 7.

The image data provided by the data storage device 3 is received by the model acquiring unit 5, which generates a vessel model based on the image data, the vessel model reflecting the vessel geometry of the subject. In particular, the vessel model is a lumen and centerline model. This vessel model is provided to the position determination unit 6, which determines a set of positions for fractional flow reserve measurements based thereon. The position determination unit 6 provides a plurality of simulations using a lumped parameter model for computational fluid dynamics. The stability of a solution is tested by varying pressure values at different positions in the model vessel tree, such that the stability of the solution can be tested by analyzing the overall variation of the solution. In this context, the position determination unit 6 takes into account information on a position and a degree of a stenosis in the vessel of the subject.

The position determination unit 6 arrives at a set of positions at which pressure measurements should be performed most optimally to deliver a stable and complete functional tree characterization of the vessel (tree) of the subject. This information is forwarded to the output unit 7.

The output unit 7 registers the vessel model (vessel tree) to one or more invasive angiograms obtained in the context of the intervention. Here, the vessel tree is overlaid onto a projection during the intervention, such that the measurement positions are displayed to the practitioner by means of the display device 4.

Figure 2:
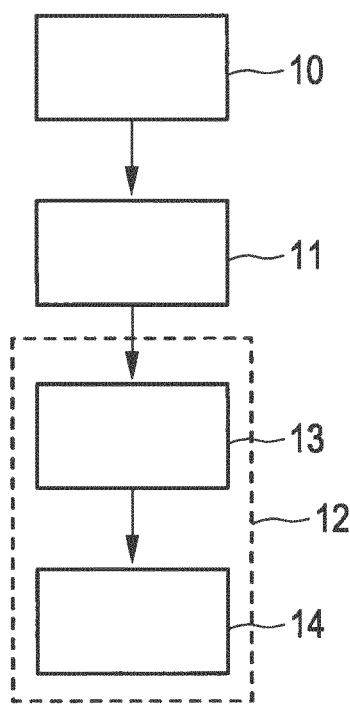
FIG. 2 shows a flow diagram illustrating an assistance method in accordance with another embodiment of the invention.

FIG. 2 shows a flow diagram illustrating an assistance method in accordance with another embodiment of the invention.

In a model acquiring step 10, a vessel model of vessel geometry of the subject is acquired. This vessel model is used in a subsequent position determination step 11, such that a set of positions for fractional flow reserve measurements to be carried out by the practitioner are determined based on the vessel model complying with a predetermined metric. In a following output step 12, the determined set of positions is outputted to the practitioner. This includes a registering step 13 in which the segmented vessel tree (obtained in the model acquiring step 10) is registered to one or more angiograms obtained in the context of the invention. Following this, in an overlay and display step 14, the vessel tree is overlaid onto a projection shown to the practitioner during the intervention, such that the determined measurement positions (determined in the position determination step 11) are displayed to the practitioner.

Figure 3:
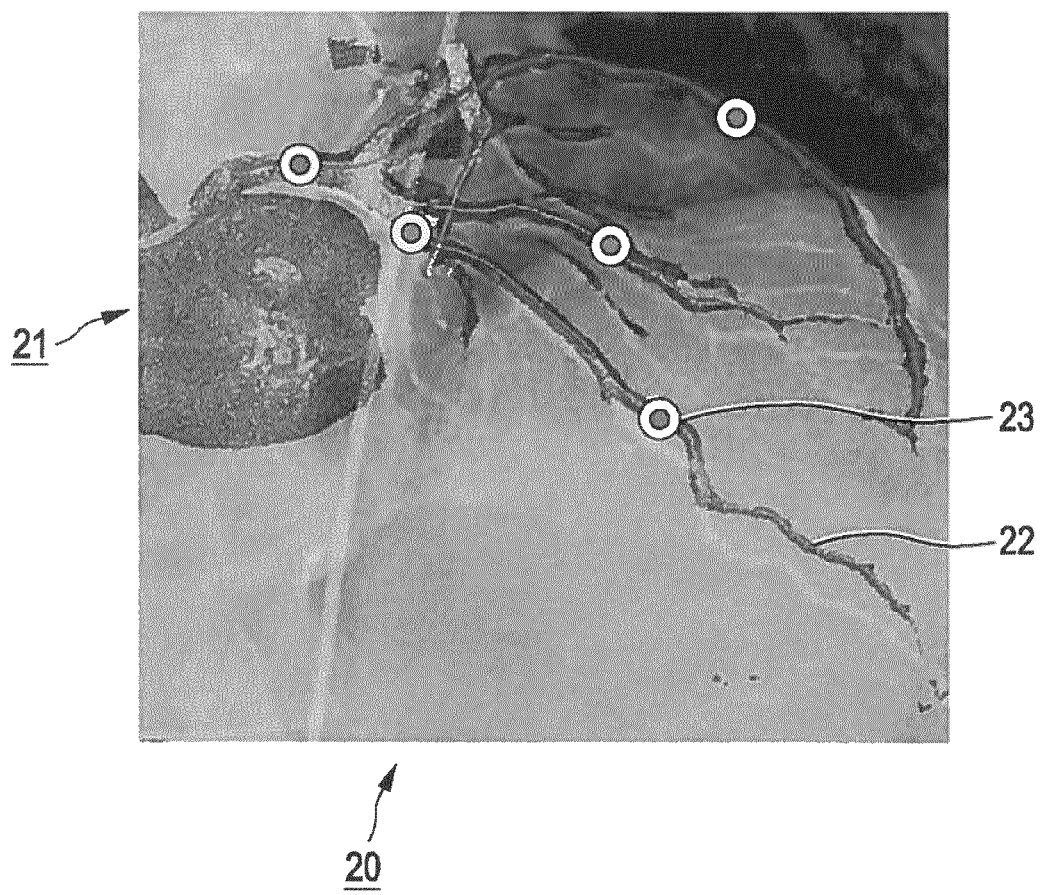
FIG. 3 shows an exemplary X-ray angiogram with a vessel tree overlay from CT and marked measurement positions for pressure measurement in accordance with the invention.

FIG. 3 shows an exemplary X-ray angiogram with a vessel tree overlay from CT and marked measurement positions for pressure measurement in accordance with the invention.

The display of the X-ray angiogram 20 is supplemented by a display of a vessel tree including the heart 21 and blood vessels 22 of the subject, wherein this information is based on the vessel model acquired. In the same display, measurement positions 23 are indicated, such that the practitioner may carry out the interventional fractional flow reserve measurement accordingly.

The ideal measurement points are supposed to provide the simulation with optimal input information to provide results with high consistency. Depending on the vessel shape it might be advantageous to measure pressure values at two positions in a single vessel segment without bifurcations. With an appropriate narrowing in the vessel geometry this could be used to determine flow values with higher accuracy than in other vessels, where these two pressure values might be redundant.

If pressure values are measured after multiple bifurcations one does not need to rely on heuristic assumptions of a scaling law to determine the relative flow distribution. The measurement position in the branches should not be arbitrary since e.g. further branching or a local narrowing may influence the result.

Also if a specific segment of the tree is under investigation its position in the vessel tree can determine in which additional branches pressure measurements are important and in which additional branches have little impact on the segment under investigation.

Finally for a single measurement to classify a stenosis a unfavorable measurement position may lead to false results, since other effects (e.g. branching or a general narrowing in distal vessels) may influence the measurement. An optimal measurement position would avoid other fluid dynamical effects to influence the targeted measurement.

In an implementation (not illustrated), in a first step, a pre-interventional CT (MR, 3DCA) data set is segmented, delivering a lumen and centerline model. In a further step, based on the vessel geometry the positions are calculated, at which pressure measurements should be performed most optimally to deliver a stable and complete functional vessel tree characterization. This is achieved by a number of test simulations using a lumped parameter model for CFD calculation together with model boundary conditions. The stability of the solution is tested by varying pressure values at different positions in the vessel tree and testing the stability of the solution by analyzing the overall variation of the solution. In addition, the segmentation accuracy may be a boundary condition for this analysis. The number of branches, the position of the branching points and the position of stenosis will also determine the measurement positions. Further, at the beginning of the actual intervention the segmented vessel tree is registered to one or more invasive angiograms and subsequently, the vessel tree is overlaid onto the projection during the intervention and the pre-calculated measurement positions are displayed. As a result, a complete functional characterization of the vessel tree including pressure, flow and resistance data are achieved.

In a modification of this implementation, in addition to just spatial measurement advice, temporal advice may also be given, e.g. by analyzing the projection sequence with respect to the cardiac phase (e.g. by correlation of the 3D model to the 2D projection or via the ECG).

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

Such variations include, for example, giving advice about measurement time and/or position in any other application (besides fractional flow reserve) where hemodynamic parameters (e.g. pressure or flow) are interventionally measured, and where a vessel model can be constructed to predict these optimal measurements through fluid dynamic simulations.

In the claims, the word "comprising" does not exclude other elements or steps, and the indefinite article "a" or "an" does not exclude a plurality.

A single processor, device or other unit may fulfill the functions of several items recited in the claims. The mere fact that certain measures are recited in mutually different dependent claims does not indicate that a combination of these measures cannot be used to advantage.

Operations like acquiring, determining, outputting, providing, obtaining, calculating, simulating, receiving, and registering can be implemented as program code means of a computer program and/or as dedicated hardware.

A computer program may be stored and/or distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. An assistance device for assisting a practitioner in an interventional hemodynamic measurement on a subject, comprising:
   a memory that stores a plurality of instructions; and
   processor circuitry that couples to the memory and that is configured to execute the plurality of instructions to:
      acquire a vessel tree model of vessel geometry of the subject;

determine a set of positions in a vessel tree for the interventional hemodynamic measurement based on the vessel tree model complying with a predetermined metric, each position in the set of positions for the interventional hemodynamic measurement is a hemodynamic parameter measurement position that indicates where at least one hemodynamic parameter is to be measured, wherein the vessel tree includes a main vessel; a branching point connected to the main vessel; a first vessel branch connected to the main vessel via the branching point; and a second vessel branch connected to the main vessel via the branching point; and cause a display to simultaneously display:
  the main vessel of the vessel tree, the branching point of the vessel tree the first vessel branch of the vessel tree and the second vessel branch of the vessel tree;
  at one of the main vessel, the branching point, the first vessel branch, and the second vessel branch, a first hemodynamic parameter measurement position of the hemodynamic parameter measurement positions; and
  at another of the main vessel, the branching point, the first vessel branch, and the second vessel branch a second hemodynamic parameter measurement position of the hemodynamic parameter measurement positions.

2. The assistance device according to claim 1, wherein the processor circuitry is further configured to provide a plurality of simulations using a lumped parameter model for computational fluid dynamics and the metric includes a stability of a solution including a set of positions.

3. The assistance device according to claim 2, wherein the processor circuitry is further configured to obtain the stability of a solution by providing simulated pressure variations and/or flow variations at a plurality of positions in the vessel tree model.

4. The assistance device according to claim 1, wherein the processor circuitry is further configured to take into account information on a position and/or degree of a stenosis in the vessel of the subject.

5. The assistance device according to claim 1, wherein the predetermined metric includes a plurality of positions included in the hemodynamic parameter measurement positions.

6. The assistance device according to claim 1, wherein the processor circuitry is further configured to determine temporal information for at least one of the hemodynamic parameter measurement positions, the temporal information indicating a measurement time in relation to a predetermined reference.

7. The assistance device according to claim 6, wherein the predetermined reference is a cardiac phase of the subject.

8. The assistance device according to claim 1, wherein the processor circuitry is further configured to receive three-dimensional image data and/or a plurality of two-dimensional image data of the vessel geometry of the subject and to generate the vessel tree model based on the image data.

9. The assistance device according to claim 8, wherein the processor circuitry is further configured to receive a pre-interventional data set of the vessel geometry of the subject and to segment the data set for generating the vessel tree model.

10. The assistance device according to claim 1, wherein the vessel tree model is a lumen and centerline model.

11. The assistance device according to claim 1, wherein the processor circuitry is further configured to register the vessel tree model with one or more invasive angiograms and to cause the display to display the hemodynamic parameter measurement positions in an overlay onto a projection during intervention.

12. An assistance system for assisting a practitioner in an interventional hemodynamic measurement on a subject, comprising:
  the assistance device according to claim 1 and at least one of
    a data storage device storing image data of vessel geometry of the subject and
    the display, wherein the display is configured to display the hemodynamic parameter measurement positions to the practitioner.

13. An assistance method for assisting a practitioner in an interventional hemodynamic measurement on a subject, comprising:
  acquiring a vessel tree model of vessel geometry of the subject;
  determining a set of positions in a vessel tree for the interventional hemodynamic measurement based on the vessel tree model complying with a predetermined metric, each position in the set of positions for the interventional hemodynamic measurement is a hemodynamic parameter measurement position that indicates where at least one hemodynamic parameter is to be measured, wherein the vessel tree includes: a main vessel; a branching point connected to the main vessel; a first vessel branch connected to the main vessel via the branching point; and a second vessel branch connected to the main vessel via the branching point; and
  causing a display to simultaneously display:
    the main vessel of the vessel tree, the branching point of the vessel tree, the first vessel branch of the vessel tree and the second vessel branch of the vessel tree;
    at one of the main vessel, the branching point, the first vessel branch, and the second vessel branch, a first hemodynamic parameter measurement position of the hemodynamic parameter measurement positions; and
    at another of the main vessel, the branching point the first vessel branch, and the second vessel branch, a second hemodynamic parameter measurement position of the hemodynamic parameter measurement positions.

14. A non-transitory computer-readable medium having one or more executable instructions stored thereon which, when executed by at least one processor, cause the at least one processor to perform an assistance method for assisting a practitioner in an interventional hemodynamic measurement on a subject, comprising:
  acquiring a vessel tree model of vessel geometry of the subject;
  determining a set of positions in a vessel tree for the interventional hemodynamic measurement based on the vessel tree model complying with a predetermined metric, each position in the set of positions for the interventional hemodynamic measurement is a hemodynamic parameter measurement position that indicates where at least one hemodynamic parameter is to be measured, wherein the vessel tree includes: a main vessel; a branching point connected to the main vessel; a first vessel branch connected to the main vessel via the branching point; and a second vessel branch connected to the main vessel via the branching point; and causing a display to simultaneously display:
- the main vessel of the vessel tree, the branching point of the vessel tree, the first vessel branch of the vessel tree, and the second vessel branch of the vessel tree;
- at one of the main vessel, the branching point, the first vessel branch, and the second vessel branch, a first hemodynamic parameter measurement position of the hemodynamic parameter measurement positions; and
- at another of the main vessel, the branching point, the first vessel branch, and the second vessel branch, a second hemodynamic parameter measurement position of the hemodynamic parameter measurement positions.

* * * * *